(12) United States Patent
Haceb

(10) Patent No.: US 11,892,590 B2
(45) Date of Patent: Feb. 6, 2024

(54) TIGHT RESERVOIR FLUID CHARACTERIZATION BY USING SONIC SLOWNESS WELL LOGS

(71) Applicant: Saudi Arabian Oil Company, Dhahran (SA)

(72) Inventor: Mohamed Amine Haceb, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 175 days.

(21) Appl. No.: 17/173,360

(22) Filed: Feb. 11, 2021

(65) Prior Publication Data

US 2022/0252756 A1 Aug. 11, 2022

(51) Int. Cl.
*G01V 1/50* (2006.01)
*G01V 5/12* (2006.01)
(Continued)

(52) U.S. Cl.
CPC ............... *G01V 5/12* (2013.01); *E21B 49/00* (2013.01); *E21B 49/02* (2013.01); *E21B 49/087* (2013.01);
(Continued)

(58) Field of Classification Search
CPC .. G01V 5/12; G01V 5/10; E21B 49/00; E21B 49/02; E21B 49/087; E21B 2200/20; G01N 24/081; G01N 33/24
See application file for complete search history.

(56) References Cited

U.S. PATENT DOCUMENTS

2005/0254343 A1\* 11/2005 Saiki ...................... G01V 1/36
367/31
2010/0309748 A1 12/2010 Tang et al.
(Continued)

FOREIGN PATENT DOCUMENTS

WO WO-2009075667 A2 \* 6/2009 ............. E21B 44/00
WO WO-2018067119 A1 \* 4/2018 ............. G01V 1/282

OTHER PUBLICATIONS

Srinivasa Rao Narhari; Bashar Al-Qadeeri; Vijaya Kidambi; Qasem Dashti; Josimar Josimar Silva; Sagnik Dasgupta; Andrew Hannan; Milton Walz; Lee Lu; Charles Wagner, "A Case Study of Prestack Orthotropic Avaz Inversion for Fracture Characterization of a Tight Deep Carbonate Reservoir of Kuwait," 2014. (Year: 2014).\*
(Continued)

*Primary Examiner* — John E Breene
*Assistant Examiner* — Christine Y Liao
(74) *Attorney, Agent, or Firm* — Fish & Richardson P.C.

(57) ABSTRACT

Some implementations of the present disclosure provide a method that include: accessing a plurality of measurement logs taken from more than one well locations of a reservoir, wherein the plurality of measurement logs encode, for each well location, a plurality of parameters; based on applying a petrophysical model to the plurality of measurement logs, determining the plurality of parameters; based on a portion of the plurality of parameters, calculating a compressional formation slowness and a shear formation slowness; and predicting a fluid type at the more than one well locations of the reservoir based on combining the compressional formation slowness and the shear formation slowness with at least one of the plurality of parameters.

18 Claims, 8 Drawing Sheets

(51) Int. Cl.

| | |
|---|---|
| *G01N 33/24* | (2006.01) |
| *G01V 5/10* | (2006.01) |
| *E21B 49/00* | (2006.01) |
| *E21B 49/08* | (2006.01) |
| *E21B 49/02* | (2006.01) |
| *G01N 24/08* | (2006.01) |

(52) U.S. Cl.
CPC ........... *G01N 24/081* (2013.01); *G01N 33/24* (2013.01); *G01V 5/10* (2013.01); *E21B 2200/20* (2020.05)

(56) References Cited

U.S. PATENT DOCUMENTS

| | | | |
|---|---|---|---|
| 2011/0255371 A1 | 10/2011 | Jing et al. | |
| 2012/0147704 A1* | 6/2012 | Xian | G01V 1/50 367/73 |
| 2013/0345983 A1* | 12/2013 | Guo | G01V 5/104 702/8 |
| 2016/0341834 A1* | 11/2016 | Bartetzko | G01V 1/50 |
| 2019/0154856 A1* | 5/2019 | Valero | G01V 1/46 |
| 2019/0293815 A1* | 9/2019 | Jocker | G01V 1/46 |

OTHER PUBLICATIONS

Ensley, "Evaluation of direct hydrocarbon indicators through comparison of compressional and shear wave data," Geophysics, Jan. 1985, 50(1):37-48.

Ferguson et al., "Reservoir indicator using Vp/Vs value derived from Broad-band 3-D seismic data," Annual Meeting of SEG, Tulsa, OK, 1996, 4 pages.

Hamada, "Reservoir fluids identification using Vp/Vs ratio," Oil & Gas Science and Technology—Rev.IFP, 2004, 59(6):649-654.

Hamada, "Vp/Vs Identify Reservoir Fluids Type," presented at the Offshore Mediterranean Conference and Exhibition, Ravenna, Italy, Mar. 28-30, 2007, 10 pages.

Pardus et al., "Vp/Vs and lithology in carbonates rocks: A Case Study in the Scipio Trend in Southern Michigan," Geophysics, 47, 4 pages.

Souder, "Using sonic logs to predict fluid type," Society of Petrophysicists and Well Log Analysts (SPLWA), Petrophysics, Sep.-Oct. 2002, 43(5):412-419.

Wyllie et al., "Elastic wave velocities in heterogeneous and porous media," Geophysics, Jan. 1956, 21(1):41-70.

* cited by examiner

TIGHT RESERVOIR FLUID CHARACTERIZATION BY USING SONIC SLOWNESS WELL LOGS

TECHNICAL FIELD

This disclosure generally relates to reservoir characterization in the context of geo-exploration for oil and gas.

BACKGROUND

Accurate reservoir characterization can be instrumental in developing, monitoring, and managing a reservoir and optimizing production. For example, porosity characterization can be instrumental in general lithology.

SUMMARY

In one aspect, some implementations provide a computer-implemented method including: accessing a plurality of measurement logs from more than one well locations of a reservoir, wherein the plurality of measurement logs encode, for each well location, a plurality of parameters; based on applying a petrophysical model to the plurality of measurement logs, determining the plurality of parameters; based on a portion of the plurality of parameters, calculating a compressional formation slowness and a shear formation slowness; and predicting a fluid type at the more than one well locations of the reservoir based on combining the compressional formation slowness and the shear formation slowness with at least one of the plurality of parameters.

Implementations may provide one or more of the following features.

The plurality of parameters may include: a bulk density, and a resistivity. The plurality of measurement logs may be based on gamma ray measurements performed at the more than one well locations of the reservoir. Combining the compressional formation slowness and the shear formation slowness with at least one of the plurality of parameters may include: cross plotting a parameter from the plurality of parameters with a metric that is based on the compressional formation slowness and the shear formation slowness. The metric may include a ratio of the compressional formation slowness and the shear formation slowness. Predicting a fluid type at the more than one well locations of the reservoir may include: performing a classification of the fluid type based on the cross plotting. The classification of the fluid type may be performed without determining an elastic rock property or a seismic velocity.

The method may further include: calibrating at least one the plurality of parameters to core sample measurements, wherein the core sample measurements comprise: a porosity measurement, and a saturation measurement, and wherein the core sample measurements are based on nuclear magnetic resonance (NMR) of core samples taken at the more than one well locations of the reservoir. The method may further include: applying one or more environmental corrections to the plurality of measurement logs before applying the petrophysical model to the plurality of measurement logs.

In another aspect, some implementations provide computer system comprising one or more processors configured to perform operations of: accessing a plurality of measurement logs from more than one well locations of a reservoir, wherein the plurality of measurement logs encode, for each well location, a plurality of parameters; based on applying a petrophysical model to the plurality of measurement logs, determining the plurality of parameters; based on a portion of the plurality of parameters, calculating a compressional formation slowness and a shear formation slowness; and predicting a fluid type at the more than one well locations of the reservoir based on combining the compressional formation slowness and the shear formation slowness with at least one of the plurality of parameters.

Implementations may include one or more of the following features.

The plurality of parameters may include: a bulk density, and a resistivity. The plurality of measurement logs may be based on gamma ray measurements performed at the more than one well locations of the reservoir. Combining the compressional formation slowness and the shear formation slowness with at least one of the plurality of parameters may include: cross plotting a parameter from the plurality of parameters with a metric that is based on the compressional formation slowness and the shear formation slowness. The metric may include a ratio of the compressional formation slowness and the shear formation slowness. Predicting a fluid type at the more than one well locations of the reservoir may include: performing a classification of the fluid type based on the cross plotting. The classification of the fluid type may be performed without determining an elastic rock property or a seismic velocity.

The operations may further include: calibrating at least one the plurality of parameters to core sample measurements, wherein the core sample measurements comprise: a porosity measurement, and a saturation measurement, and wherein the core sample measurements are based on nuclear magnetic resonance (NMR) of core samples taken at the more than one well locations of the reservoir. The operations may further include: applying one or more environmental corrections to the plurality of measurement logs before applying the petrophysical model to the plurality of measurement logs.

In yet another aspect, some implementations provide a non-transitory computer-readable medium comprising software instructions that, when executed by a computer processor, cause the computer processor to perform operations of: accessing a plurality of measurement logs from more than one well locations of a reservoir, wherein the plurality of measurement logs encode, for each well location, a plurality of parameters; based on applying a petrophysical model to the plurality of measurement logs, determining the plurality of parameters; based on a portion of the plurality of parameters, calculating a compressional formation slowness and a shear formation slowness; and predicting a fluid type at the more than one well locations of the reservoir based on combining the compressional formation slowness and the shear formation slowness with at least one of the plurality of parameters.

Implementations may include one or more of the following features.

Combining the compressional formation slowness and the shear formation slowness with at least one of the plurality of parameters may include: cross plotting a parameter from the plurality of parameters with a metric that is based on the compressional formation slowness and the shear formation slowness. Predicting a fluid type at the more than one well locations of the reservoir may include: performing a classification of the fluid type based on the cross plotting.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

DESCRIPTION OF DRAWINGS

Like reference numbers and designations in the various drawings indicate like elements.

DETAILED DESCRIPTION

Figure 1:
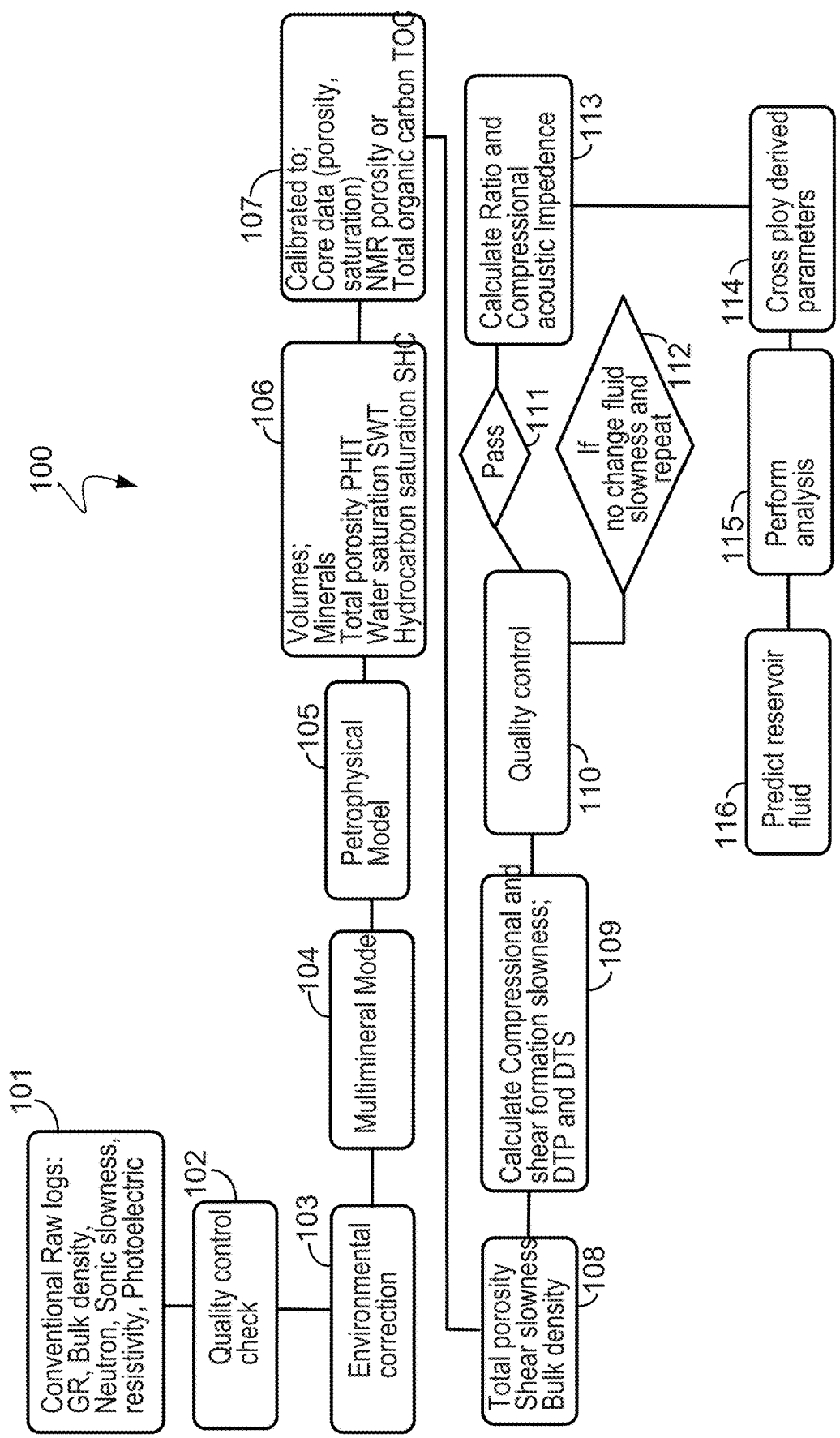
FIG. 1 shows an example of a flow chart for predicting reservoir fluid base in part on reservoir fluid characterization according to an implementation of the present disclosure.

Accurate reservoir characterization can be instrumental in developing, monitoring, and managing a reservoir and optimizing production. The disclosed technology is directed to a computerized method that integrates parameters derived from sonic slowness that corresponds to known reservoir fluid and matrix. In some implementations, the derived parameters are cross-plotted and interpreted to characterize the tight reservoir pores fluid. Both the transmit time of the compressional and shear waves and the compression time of the shear wave are affected by the density and elasticity properties of the rock. The transit time of the compressional wave (P wave) is more sensitive to fluid changes from water to oil or gas. This transit time is greater in hydrocarbon than in water saturated reservoir. However, the transit time of shear wave (S wave) is less sensitive to fluid. In particular, minor changes may be observed when water is replaced by hydrocarbon. The sensitivity difference between the transit times of the P and S waves is attributed to the fact that compressional waves may depend on bulk modulus of the rock while the shear waves may be mainly related to the density decrease. Some implementations may advantageously leverage cross plotting the ratio and compressional acoustic impedance to compare and contrast with other intrinsic rock parameters to distinguish between different fluid categories (oil, gas and water). Implementations demonstrate that such results can be later confirmed from well field test data.

The implementations can determine the type of the pores saturated fluids in unconventional reservoir without using the seismic velocity or required elastic rock properties. While conventional reservoirs with produced formation free water may be analyzed using, the ratio of $V_P/V_S$, implementations described by the present disclosure are based on cross plot domain and designated for unconventional reservoir Where there is no free water all is bounded or irreducible (source rock) or very low water cut in tight reservoir. For context, conventional reservoir includes both hydrocarbon and free formation water. Unconventional reservoir, however, can be characterized by tight sand with good porosity. Although analysis can produce hydrocarbon and formation water with very low water cut after perforation or fracking, the unconventional reservoir is not source rock. Here, unconventional source rock reservoir can include carbonates embedded in rich mud stones where porosity is located in the kerogen and the formation water is irreducible/connate or bounded that may not be produced after fracking the reservoir. Therefore, the water produced on the surface may only be the injected frack fluid and no formation water can be confirmed by salinity or radioactive tracers.

The terminology used in the present disclosure includes the following terms.

The term "slowness" refers to a quantity introduced in seismology which is the reciprocal of velocity. Thus travel time of a wave is the distance that the wave travels times the slowness of the medium. Thus, Slowness=1/Velocity. Moreover, the term "sonic slowness" and the term "acoustic travel time" are the same. Both terms represent the time spent by the sound or an acoustic wave to travel a certain distance, typically from a transmitter to a receiver across the formation. This time interval is proportional to the reciprocal of the velocity. The travel time or the slowness can be used to calibrate the seismic data and are often combined with density to create synthetic seismogram.

The term "machine learning analytics" refers to the use of machine learning and applied statistics to predict unknown conditions based on the available data. Two general areas that fall under machine learning analytics are classification and regression. While classification refers to the prediction of categorical values, regression connotes the prediction of continuous numerical values. One machine learning implementation is also known as "supervised learning" where the "correct" target or y values are available. For illustration, the goal of some implementations is to learn from the available data to predict the unknown values with some defined error metrics. In supervised learning, for example, there are a set of known predictors (features) $x_1, x_2, \ldots, x_m$ which are known to the system as well as the target values $y_1, y_2, \ldots, y_n$, which are to be inferred. The system's objective is to train a machine learning model to predict new target values $y_1, y_2, \ldots, y_n$ by observing new features.

The implementations can employ a variety of machine learning algorithms. For classification, examples of prediction algorithms can include, logistic regression, decision trees, nearest neighbor, support vector machines, K-means clustering, boosting, and neural networks. For regression, examples of predication algorithms can include least squares regression, Lasso, and others. The performance of an algorithm can depend on a number factors, such as the selected set of features, training/validation method and hyper-parameters tuning. As such, machine learning analytics can manifest as an iterative approach of knowledge finding that includes trial and error. An iterative approach can iteratively modify data preprocessing and model parameters until the result achieves the desired properties.

Referring to FIG. 1, a workflow diagram 100 is shown as an example. The workflow may initially access conventional raw log data (101). The raw log data may include: the neutron log, log of bulk density measurement, log of sonic slowness measurement, log of resistivity measurement, and log of photoelectric measurement.

The neutron log is sensitive mainly to the amount of hydrogen atoms in a formation. The tool operates by bombarding the formation with high energy neutrons. These neutrons undergo scattering in the formation, losing energy and producing high energy gamma rays (GRs). The scattering reactions occur most efficiently with hydrogen atoms. The resulting low energy neutrons or gamma rays can be detected as measurement log data, and their count rate is related to the amount of hydrogen atoms in the formation. In formations with a large amount of hydrogen atoms, the neutrons are slowed down and absorbed very quickly and in a short distance. The count rate of slow neutrons or capture gamma rays is low in the tool. Hence, the count rate will be low in high porosity rocks. In formations with a small amount of hydrogen atoms, the neutrons are slowed down and absorbed more slowly and travel further through the rock before being absorbed. The count rate of slow neutrons or capture gamma rays in the tool is therefore higher. Hence, the count rate will be higher in low porosity rocks.

The other logs may likewise be based on gamma ray (GR) measurements. For example, the density log can leverage the fact that gamma ray scattering as a function of the bulk density of the, irradiated matrix. The bulk density is the overall density of the matrix and the fluids (water, oil, gas) within the pores. A gamma ray source irradiates a stream of gamma rays into the formation, some of which are adsorbed, some passed on through the matrix, and some scattered. The ability of the matrix to attenuate the gamma rays is recorded as the intensity of scattered gamma rays arriving at two fixed distances from the gamma ray source. Bulk density is determined by a correlation between the gamma ray intensity at the detectors and data used for calibration of the tool. The gamma ray intensity arriving at the detectors is an inverse function of the bulk density.

The logs may also analyze the low-energy region of the scattered gamma ray spectrum separately. These low-energy gamma rays are subject to photoelectric (PE) absorption, which is controlled by the atomic number of the underlying substance, in turn, strongly correlates with lithology. For example, the PE absorption cross section can be strongly dependent on the energy of the gamma rays, as well as the average atomic number.

The logs may further include resistivity logging that seeks to characterize the rock or sediment in a borehole by measuring its electrical resistivity. Resistivity is a fundamental material property which represents how strongly a material opposes the flow of electric current. In these logs, resistivity is measured using, for example, four electrical probes to eliminate the resistance of the contact leads. The log must run in holes containing electrically conductive mud or water, i.e., with enough ions present in the drilling fluid.

The logs may further include a sonic log that is an acoustic log obtained by emitting sound waves which start at the source, travel through the formation, and return back to the receiver. The travel time from the source to the receiver is called slowness and as a result sonic logs are sometimes referred to as sonic slowness logs. The formation slowness can be computed by using range of matrix values as described below in equations (1) and (2). The shear slowness log can be acquired in open hole from the sonic tool measurements because the shear does not propagate in liquid.

The workflow may then perform a quality control check (102). Based on the quality control check, outlier data can be removed or suppressed from further processing. The outlier data may include statistical outliers detected as under-represented sample, for example, samples that fall outside several standard deviations of the population mean.

The workflow may then perform environmental correction (103). The environmental correction refers to adjustments made to original log data before reservoir evaluation. Different measurements may entail different corrections. For example, resistivity measurements may need correction for the borehole, invasion and shoulder beds, and may also be corrected for apparent dip, anisotropy and surrounding beds in horizontal wells. Density measurements require correction only for borehole size, while neutron porosity measurements require corrections for temperature, pressure and a large number of borehole and formation parameters.

The workflow may then launch multi-mineral modelling (104) and perform petrophysical evaluation (105). The models may include various parameters of the reservoir, for example, volume, mineral, total porosity, water saturation, and hydrocarbon saturation (106). Total porosity may also be known as PHIT, which includes the pore space in the formation reservoir. Water saturation may include total water saturation, also known as SWT, which is the fraction of the pore space occupied by water. Hydrocarbon saturation, also known as SHC, may refer to hydrocarbon in the reservoir.

The modelled parameters may then be calibrated to data from core plug samples extracted from the reservoir (107). Such core data may include porosity data, saturation data, and total carbon. For example, such core data may be taken from NMR logging for analyzing total organic carbon (TOC). In some cases, the total porosity derived density neutron is calibrated to nuclear magnetic resonance total porosity and organic content fraction across the source rock reservoir.

Various implementations may employ the sonic slowness combined with porosity and bulk density logs to determine the reservoir fluid type. For example, the workflow may then proceed to estimate total porosity, shear slowness, and bulk density based on the calibrated data 108). Specifically, the transit time for both compressional and shear waves can be computed as shown below using Eqs. (1), and (2):

$$DTP=Dtcf*\varphi+(1-\varphi)*Dtpm \quad (1),$$

$$DTS=Dts*\varphi+(1-\varphi)*Dtsm \quad (2).$$

Here DTP, DTS respectively correspond to compressional and shear formation slowness, Dtcf is compressional fluid slowness; Dtpm, Dtsm respectively correspond to compressional and shear matrix slowness; $\varphi$ is the total porosity; and Dts is shear slowness used from log, reading as the shear waves is less sensitive to the fluid changes. Formation slowness includes both matrix and fluid slowness. Matrix slowness value is known and depend on lithology. Similarly, assuming a known fluid filled pores reservoir from logs response, fluid slowness can be determined from petrophysical analysis. In case the assumption is incorrect, the fluid type can be changed and the process repeated. Notably, DTS is the computed shear slowness determined by using Eq. (2). Respectively, the range of compressional and shear wave for limestone (LS) and sandstone (SS) matrix are:

| LS | Dtpm | 47.6-43.5 µs/ft | Dtsm | 82.29 µs/ft |
| SS | Dtpm | 55.6-51.3 µs/ft | Dtsm | 74 µs/ft |

The calculation may be subject to quality control (110). Some implementations can use the above equations (1) and (2), and the range of the compressional and shear values for limestone matrix. Assuming the reservoir fluid is water, the implementations can determine formation slowness for both compressional and shear waves only in the interval where the pores space are filled with water. In other cases, the assumption for water does not hold and reservoir fluid type need to be updated. Based on the update, the implementations can perform numerical application and display results on cross plot domain for interpretation with different fluid type. If the quality control does not indicate changes to fluid slowness, the process may repeat (112) from, for example, block 101. If the quality control passes (111), the workflow may then compute ratio of the compressional wave slowness over the shear wave slowness (113), for example, according to Eqs. (3) and (4) below:

$$RATIO = DTP/DTS \quad (3)$$

$$AIP = RHOB/DTP \quad (4),$$

where AIP is the compressional acoustic impedance, and RHOB is the formation bulk density.

Some implementations may leverage porosity derived density or data from NMR measurements rather than sonic porosity data. In cases where sonic porosity data is used, a correction may be involved to account for the fact that the sonic slowness read higher in presence of hydrocarbon or shale and lower in fractured carbonates reservoir or vugs.

The workflow may then proceed to cross plot the above derived parameters (114) Based on the cross-plots, some implementations may perform analysis (115) and predict reservoir fluid (116). As demonstrated below, implementations described by the present disclosure may provide a solution to fluid characterization in an unconventional tight reservoir where conventional petrophysical charts or standards method have failed to identify the fluid type. The deficiency of conventional charts may stem from the fact that well logs response are affected by several factors such as formation tightness, high volume of clay, organic matter content, and presence of hydrocarbon. In physics domain, the predicted model for reservoir fluids substitution may mainly be built on the pre-determined elastic rock properties extracted from velocity seismic by assuming reservoir homogeneity, moveable fluid and calibrated velocity. However, the implementations described in the present disclosure can combine the derived parameters from sonic slowness with porosity and bulk density tog to allow for prediction of the pore fluid without the need for pre-determining elastic rock properties or seismic velocity. The elastic rock properties can include a metric that measures elasticity, a metric that quantifies a stress or a strain. In other words, the disclosed implementations can operate with less uncertainty and can save time. The acoustic slowness or sonic travel time have been described and explained above. The velocity is measured by a distance over travel time. For both seismic and acoustic data, if the distance between receivers and transmitters is known, the velocity can be determined from the travel time for a wave propagate through the formation interval which is measured by the tool. In various implementations, the acoustic time may refer to the one way time.

Figure 2:
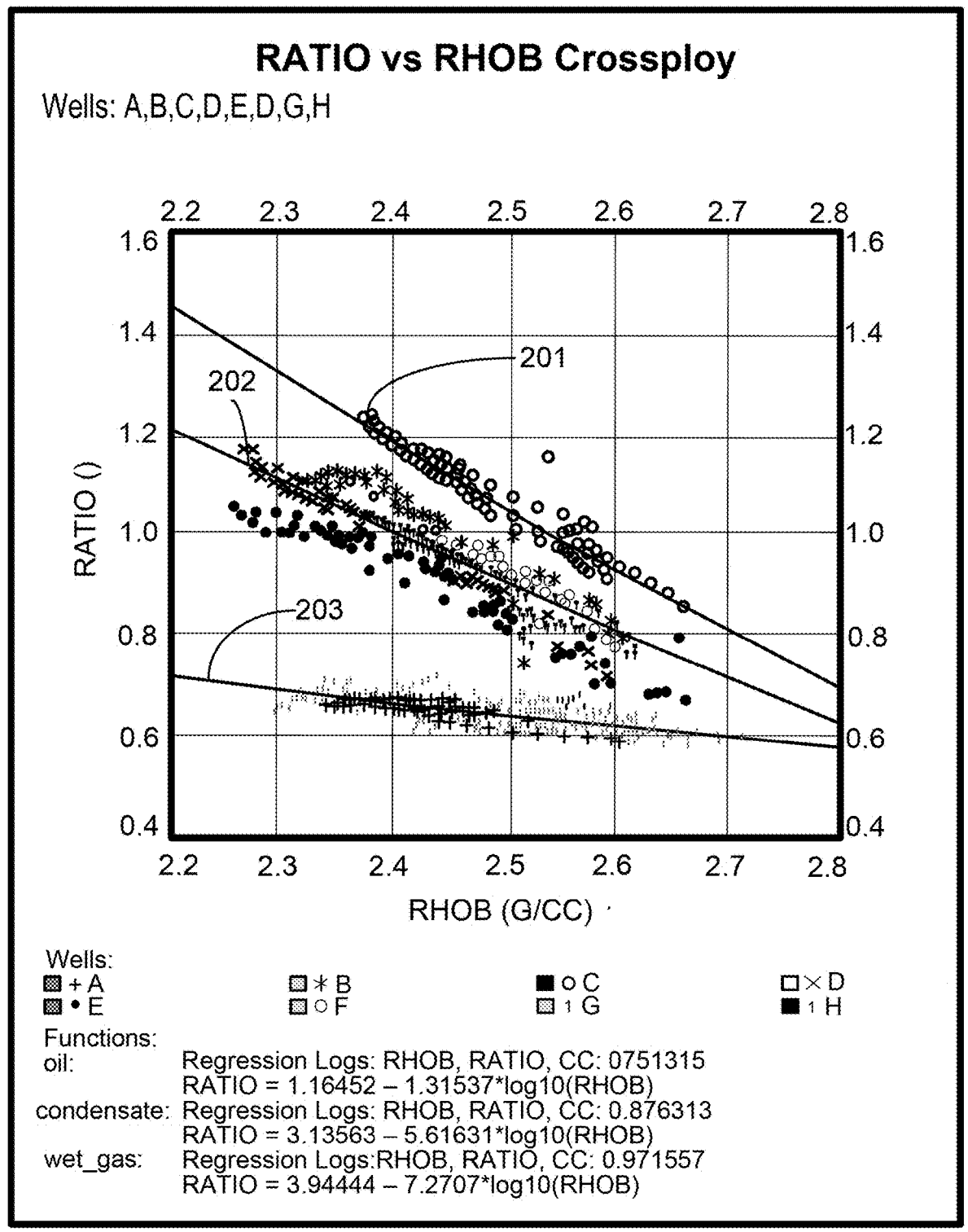
FIG. 2 is an example of a cross plot of slowness ratio as a function of bulk density according to an implementation of the present disclosure.

FIG. 2 shows an example of a cross plot of slowness ratio as a function of bulk density (RHOB) according to an implementation of the present disclosure. The example is based on data samples taken from various well locations inside a first reservoir rich in carbonates source rock. In this example, each cluster of data samples correspond to a well location. Each line of regression represents results from a regression analysis of the underlying data samples. In particular, the top line of regression (201) corresponds to a wet gas configuration; the middle line of regression (202) corresponds to a condensate configuration; and the bottom line of regression (203) corresponds to a black oil configuration. The example demonstrates a reversed relationship between the ratio and hulk density for various wells in this reservoir. In other words, the ratio decreases linearly as a function of hulk density. The example demonstrates significant increase of the ratio while the bulk density drops, indicating that fluid repartition is closely related to fluid density. In addition, both organic matter and fluid density effects are noticed on the slowness in source rock reservoir.

Figure 3B:
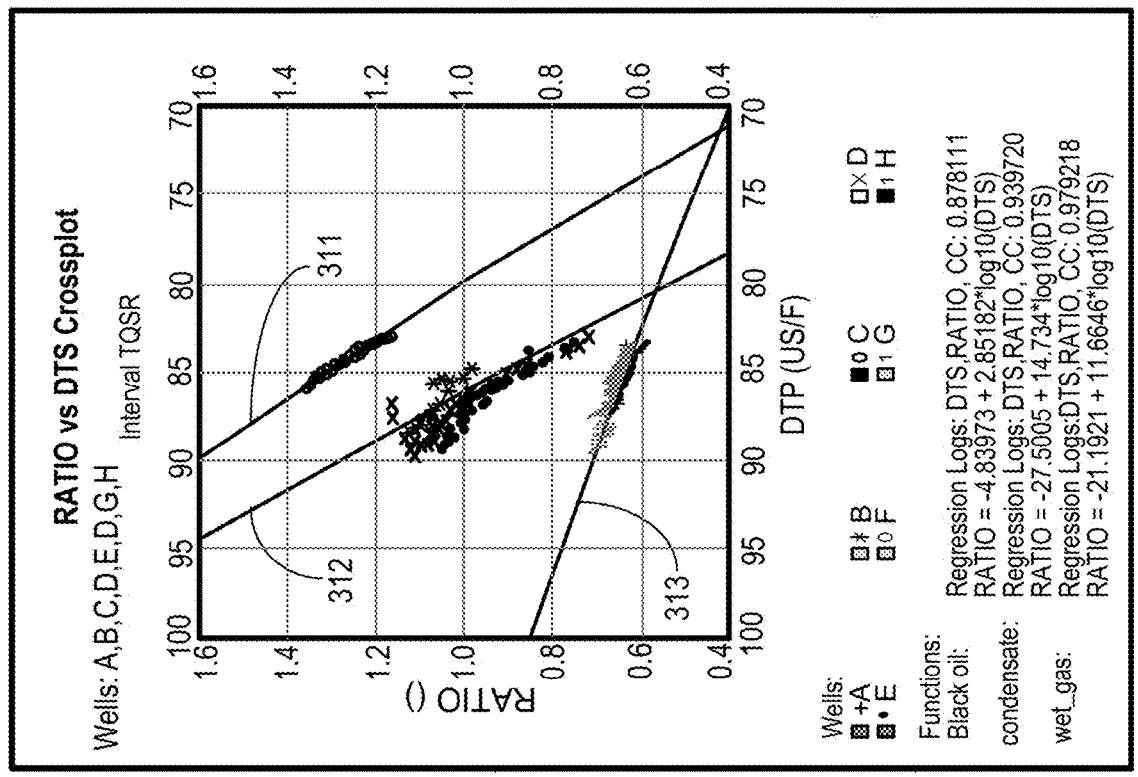
FIG. 3B is an example of a cross plot of slowness ratio versus shear formation slowness according to an implementation of the present disclosure.
Figure 3A:
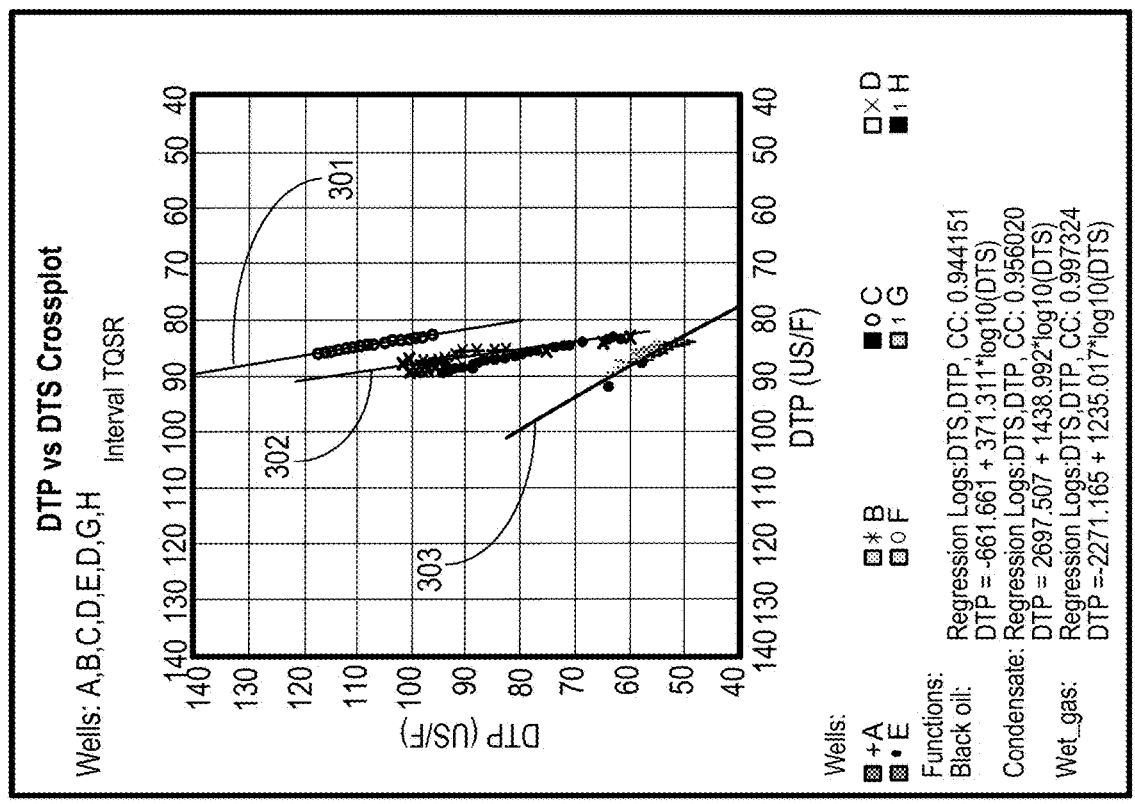
FIG. 3A is an example of a cross plot of compressional formation slowness versus shear formation slowness according to an implementation of the present disclosure.

FIG. 3A represents a cross plot of compressional formation slowness versus shear formation slowness for this first reservoir. Wet gas corresponds to the line of regression 301; condensate corresponds to the line of regression 302, and black oil corresponds to the line of regression 303. Meanwhile, FIG. 3B shows an example of a cross plot of slowness ratio versus shear formation slowness. Wet gas corresponds to the line of regression 311, condensate corresponds to the line of regression 312; and black oil corresponds to the line of regression 313. In both examples, a clear separation is observed between different fluids types across the various well locations of this reservoir, as visualized by the increases of the ratio and slight decreases of the shear slowness due to density fluid changes. Similar to FIG. 2, greater ratio of compressional and shear slowness is seem in gas-saturated rock (top line of slope) than oil-saturated rock (bottom line of slope).

Figure 4:
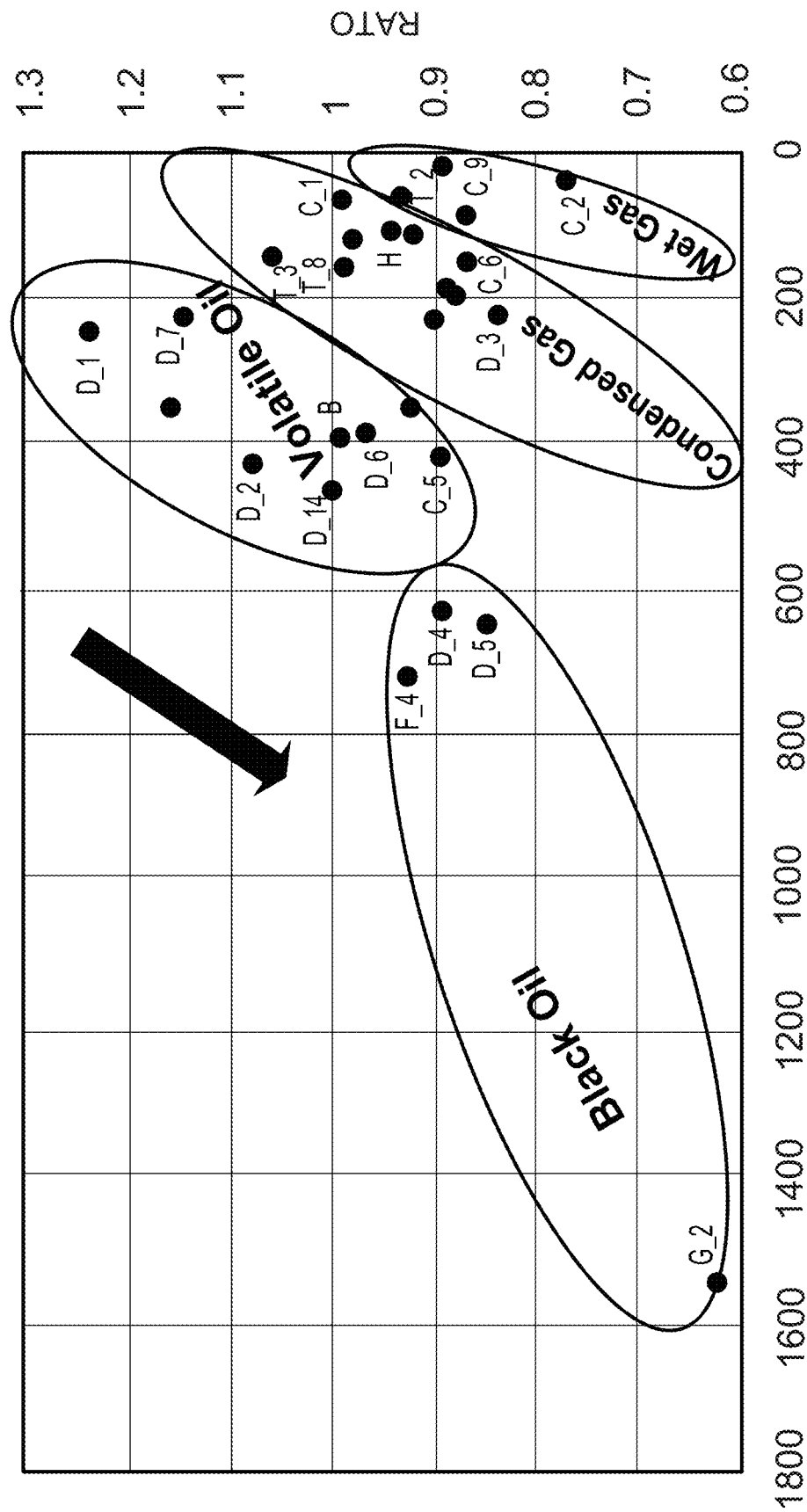
FIG. 4 is an example of a cross plot of slowness ratio versus condensed gas ratio according to an implementation of the present disclosure.

FIG. 4 is an example of a cross plot of slowness ratio versus condensed gas ratio according to an implementation of the present disclosure. The cross plot shows results of data samples from various well locations in the first reservoir. As illustrated, the cross plot demonstrates a well-defined separation between gas and liquid configurations. In fact, data samples corresponding to the black oil (low maturity) configuration tends cluster in the arrow indicated area, while data samples corresponding to more mature configurations such as the volatile oil configuration, the condensed as configuration, and wet gas configuration are more likely clustered to the right. This clustering stems from the increases of the ratio in gas window as compared to black oil (low maturity).

Figure 5B:
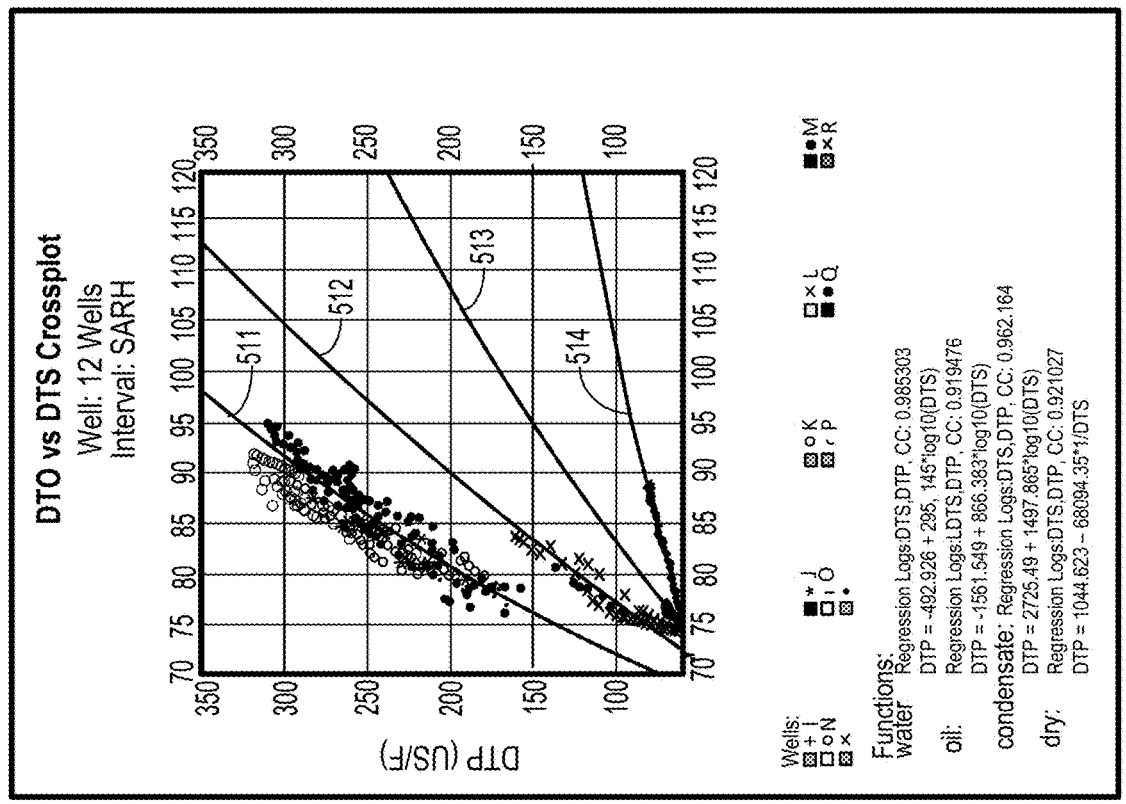
FIG. 5B is an example of a cross plot of compressional formation slowness versus shear formation slowness according to an implementation of the present disclosure.
Figure 5A:
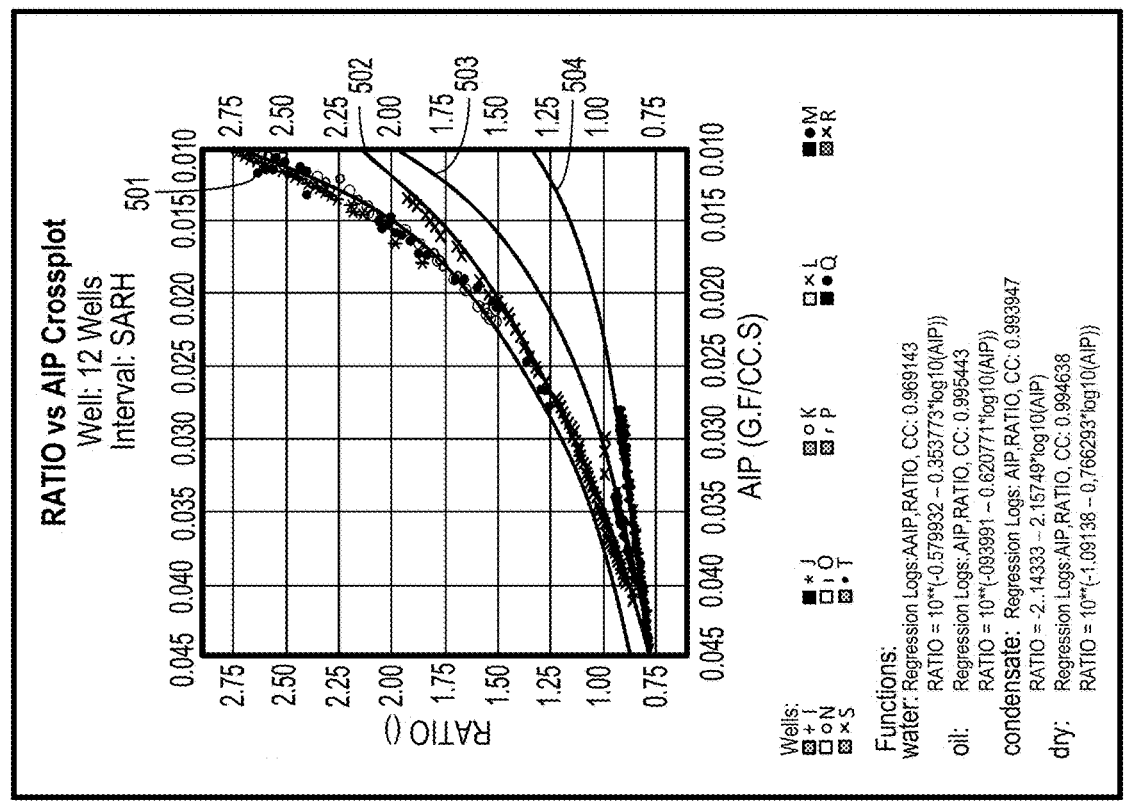
FIG. 5A is an example of a cross plot of slowness ratio versus compressional acoustic impedance according to an implementation of the present disclosure.
Figure 6:
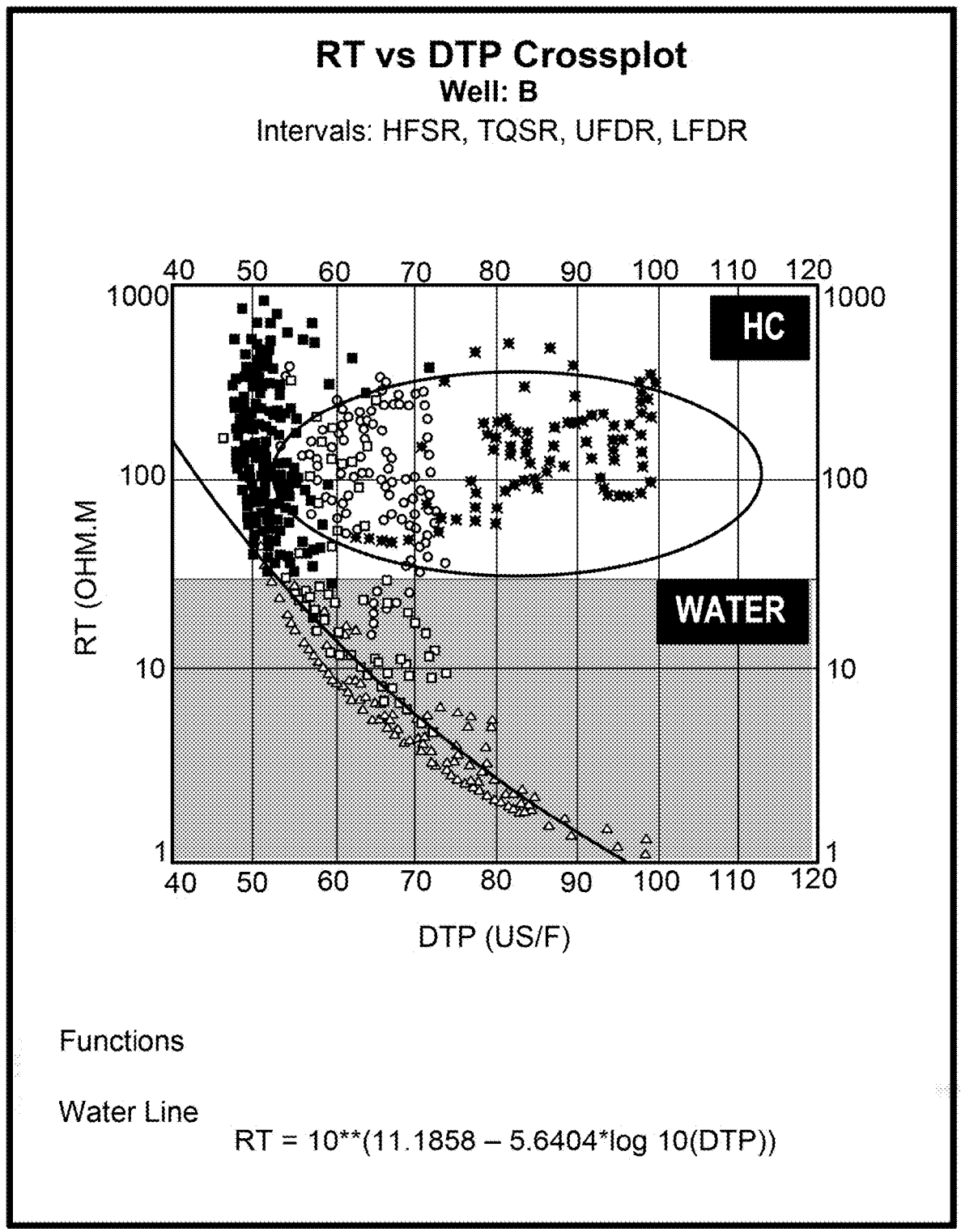
FIG. 6 shows an example of a cross plot of true formation resistivity versus compressional formation slowness according to an implementation of the present disclosure.

FIGS. 5A, 5B, and 6 show results for a second and different reservoir. FIG. 5A is an example of a cross plot of slowness ratio versus compressional acoustic impedance (AIP) according to an implementation of the present disclosure. In FIG. 5A, the cross plot demonstrates an increase for the ratio in presence of dry gas. In more detail, the data samples came from various well locations at this second reservoir. The data samples demonstrate a well-defined clustering into four regression lines, namely, lines 501, 502, 503, and 504. Line 501 shows the regression log for a dry gas configuration. Line 502 shows the regression log for a condensate configuration. Line 503 shows the regression log for a black oil configuration. Line 504 shows the regression log for a water configuration. In each case, the trend indicates an increase for the P wave slowness, accompanied by a slight drop of the shear wave's transit time due to fluid density changes. In these implementations, the regression reflects the relationship between slowness, fluid type and formation matrix. As the matrix or pores fluid is changed with respect to pores size/connectivity, the correlation is also changed. Linear, logarithmic or exponential regression is based on best fit of the displayed data. FIG. 5B is an example of a cross plot of compressional formation slowness versus shear formation slowness according to an implementation of the present disclosure. The cross plot likewise demonstrates a well-defined separation of the four configurations through four regression lines, namely, lines 511, 512, 513, and 514, which respectively correspond to a dry gas configuration a condensate configuration, a black oil configuration, and a water configuration.

FIG. 6 shows an example of true formation resistivity versus compressional wave transit time according to some implementations. This example demonstrates a well-defined separation between gas (circled region) and water below (grey highlight). This separation is partially due to significant increases of P wave slowness when resistivity drops in water saturated region. The regression in this plot indicates that the water line corresponds to low compressional slowness reading in water zone (as confirmed by low resistivity measurements) compared to the top interval of the tight source rock reservoir filled with hydrocarbon (HC) characterized by high compressional slowness reading toward the right (also confirmed by resistivity increasing). The resistivity is on a logarithmic scale displayed on linear scale with slowness and even the trend of the data is no longer linear due to the tightness and fluid type. In this example, the reservoir is tight gas source rock reservoir.

Figure 7:
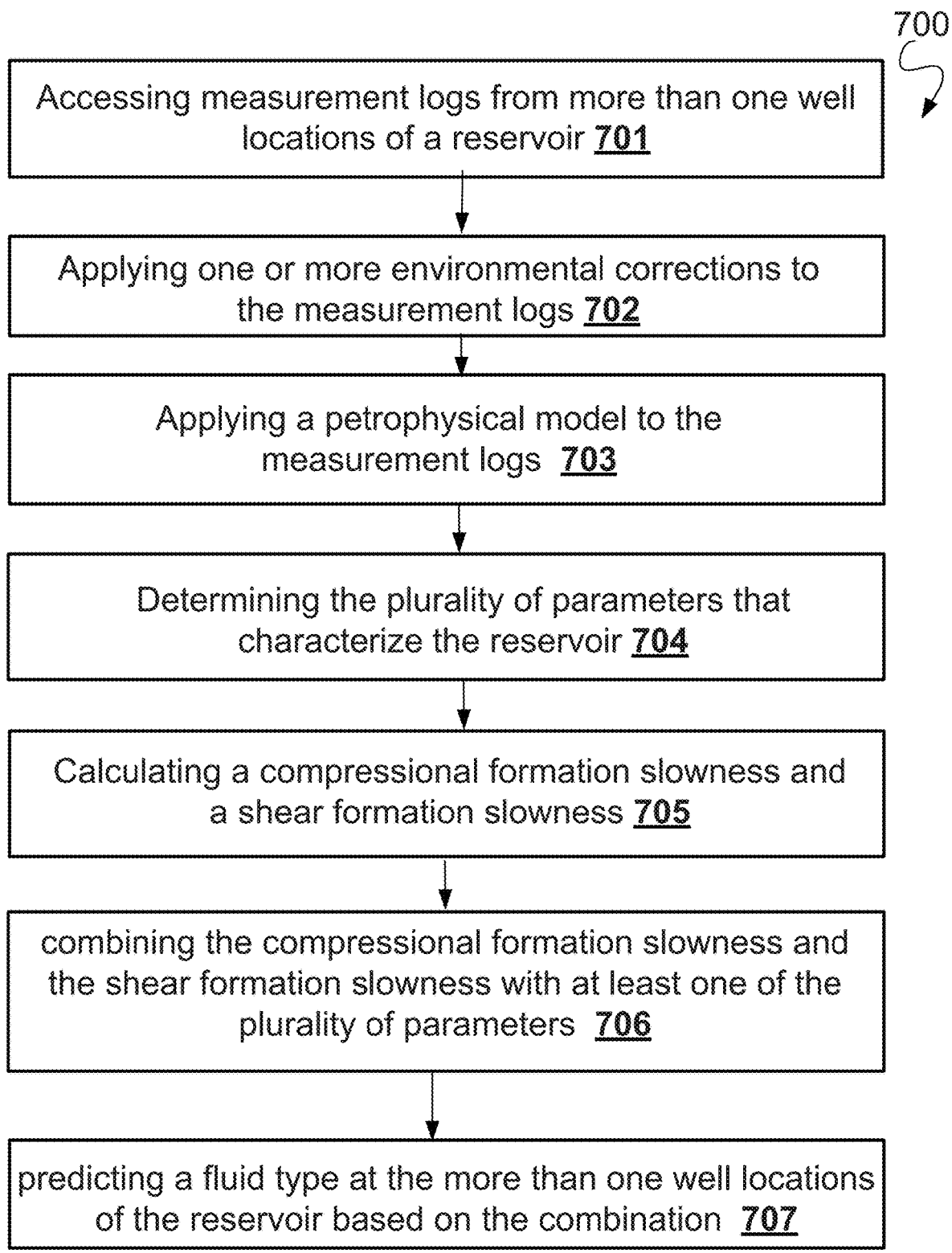
FIG. 7 is an example of a flow chart according to an implementation of the present disclosure.

As illustrated by the flow chart 700 of FIG. 7, an implementation may start with obtaining access to measurement data of a reservoir (701). The measurement data may characterize one or more features of a reservoir. For example, the measurement data may include a neutron log, a log, of bulk density measurement, a log of sonic slowness measurement, a log of resistivity measurement, and a log of photoelectric measurement. Resistivity logging that seeks to characterize the rock or sediment in a borehole by measuring its electrical resistivity. The measurement logs may be taken from multiple well locations of the reservoir.

Next, the implementations may apply one or more environmental corrections to the measurement logs (702). The environmental correction may refer to adjustments made to original log data before reservoir evaluation. Different measurements may entail different corrections. The implementations may additionally perform quality check of the measurement logs.

Thereafter, the implementations may apply a petrophysical model to the measurement logs (703). The model may characterize various parameters of the reservoir, for example, volume, mineral, total porosity, water saturation, hydrocarbon saturation. The implementations may then determine multiple parameters that characterize the reservoir (704). In these implementations, the modelled parameters may then be calibrated to data from core plug samples extracted from the reservoir. Such core data may include porosity data, and saturation data. For example, such core data may be taken from NMR logging for analyzing total organic carbon (TOC). In some cases, the total porosity derived density neutron is calibrated to nuclear magnetic resonance total porosity and organic content fraction across the source rock reservoir.

Subsequently, the implementations may calculate a compressional formation slowness and a shear formation slowness (705). In some cases, the transit time for both compressional and shear waves can be computed according to equations (1) and (2) as discussed above in association with FIG. 1.

Implementations may then proceed to combine the compressional formation slowness and the shear formation slowness with at least one reservoir parameters (706). Based on the combination, the implementations can predict a fluid type at the well locations of the reservoir (707). The implementations can perform the prediction by, for example, cross plotting a metric based on the compressional formation slowness and the shear formation slowness with a reservoir parameter. In some cases, the metric can be a ratio of the compressional formation slowness over the shear formation slowness. In some cases, the reservoir parameter can be the compressional acoustic impedance AIP, which is related to the formation bulk density. The implementations may fill the gap and without loss of accuracy. The implementations described by the present disclosure can combine metrics derived from formation slowness with porosity and bulk density log to allow for prediction of the pore fluid without the need for pre-determining, elastic rock properties or seismic velocity.

Figure 8:
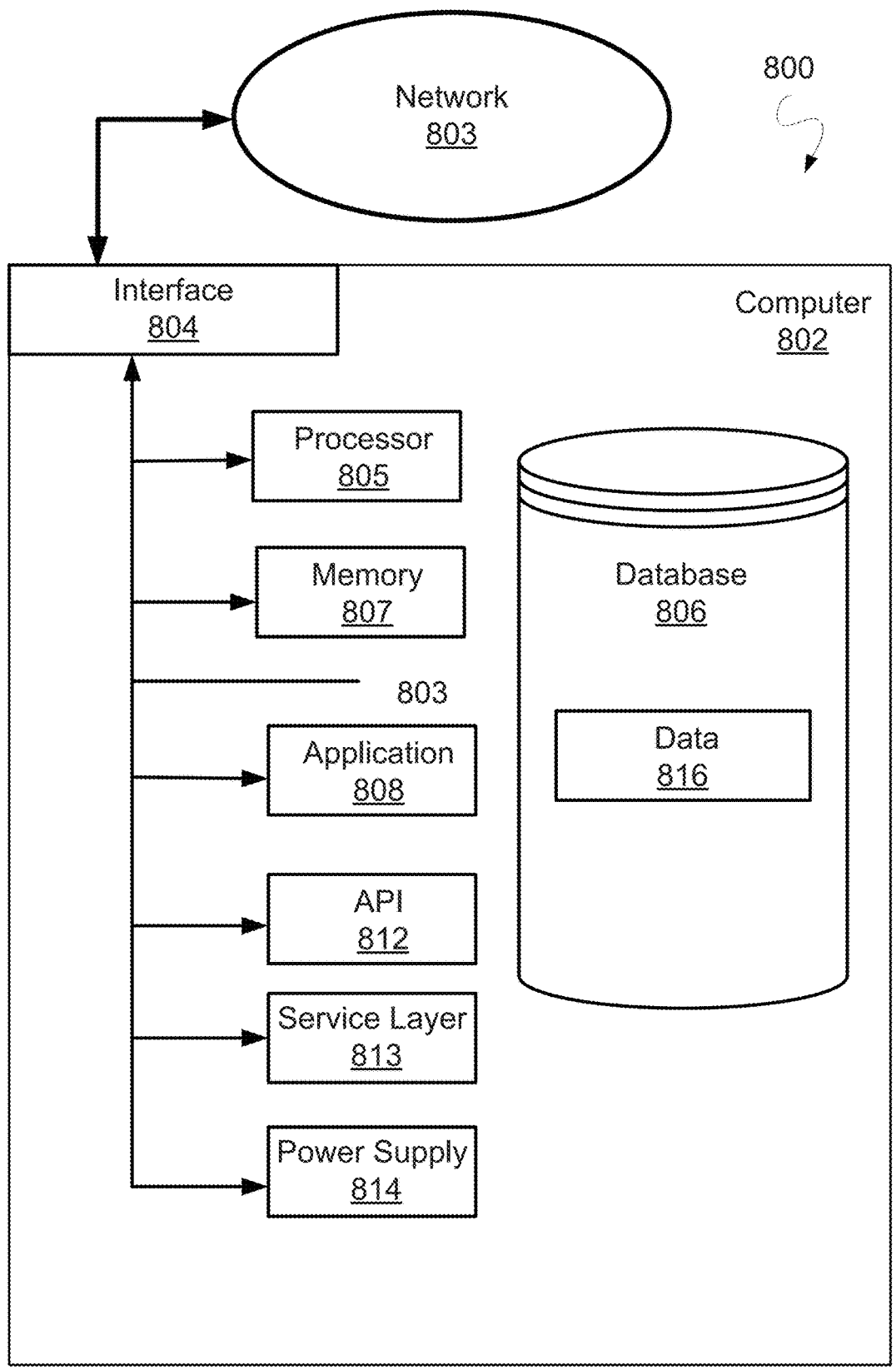
FIG. 8 is a block diagram illustrating an example of a computer system used to provide computational functionalities associated with described algorithms, methods, functions, processes, flows, and procedures, according to an implementation of the present disclosure.

FIG. 8 is a block diagram illustrating an example of a computer system 800 used to provide computational functionalities associated with described algorithms, methods, functions, processes, flows, and procedures, according to an implementation of the present disclosure. The illustrated computer 802 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 802 can comprise a computer that includes an input device, such as a keypad, keyboard, touch screen, another input device, or a combination of input devices that can accept user information, and an output device that conveys information associated with the operation of the computer 802, including digital data, visual, audio, another type of information, or a combination of types of information, on a graphical-type user interface (UI) (or GUI) or other UI.

The computer 802 can serve in a role in a computer system as a client, network component, a server, a database or another persistency, another role, or a combination of roles for performing the subject matter described in the present disclosure. The illustrated computer 802 is communicably coupled with a network 803. In some implementations, one or more components of the computer 802 can be configured to operate within an environment, including cloud-computing-based, local, global, another environment, or a combination of environments.

The computer 802 is an electronic computing device operable to receive, transmit, process, store, or manage data and information associated with the described subject matter. According to some implementations, the computer 802 can also include or be communicably coupled with a server, including an application server, e-mail server, web server, caching server, streaming data server, another server, or a combination of servers.

The computer 802 can receive requests over network 803 (for example, from a client software application executing on another computer 802) and respond to the received requests by processing the received requests using a software application or a combination of software applications. In addition, requests can also be sent to the computer 802 from internal users, external or third-patties, or other entities, individuals, systems, or computers.

Each of the components of the computer 802 can communicate using a network 803 (or system bus). In some implementations, any or all of the components of the computer 802, including, hardware, software, or a combination of hardware and software, can interface over the network 803 (or system bus) using an application programming interface (API) 812, a service layer 813, or a combination of the API 812 and service layer 813. The API 812 can include specifications for routines, data structures, and object classes. The API 812 can be either computer-language independent or dependent and refer to a complete interface, a single function, or even a set of APIs. The service layer 813 provides software services to the computer 802 or other components (whether illustrated or not) that are communicably coupled to the computer 802. The functionality of the computer 802 can be accessible for all service consumers using this service layer. Software services, such as those provided by the service layer 813, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 802, alternative implementations can illustrate the API 812 or the service layer 813 as stand-alone components in relation to other components of the computer 802 or other components (whether illustrated or not) that are communicably coupled to the computer 802. Moreover, any or all parts of the API 812 or the service layer 813 can be implemented as a child or a sub-module of another software module, enterprise application, or hardware module without departing from the scope of the present disclosure.

The computer 802 includes an interface 804. Although illustrated as a single interface 804 in FIG. 8, two or more interfaces 804 can be used according to particular needs, desires, or particular implementations of the computer 802. The interface 804 is used by the computer 802 for communicating with another computing system (whether illustrated or not) that is communicatively linked to the network 803 in a distributed environment. Generally, the interface 804 is operable to communicate with the network 803 and comprises logic encoded in software, hardware, or a combination of software and hardware. More specifically, the interface 804 can comprise software supporting one or more communication protocols associated with communications such that the network 803 or interface's hardware is operable to communicate physical signals within and outside of the illustrated computer 802.

The computer 802 includes a processor 805. Although illustrated as a single processor 805 in FIG. 8, two or more processors can be used according to particular needs, desires, or particular implementations of the computer 802. Generally, the processor 805 executes instructions and manipulates data to perform the operations of the computer 802 and any algorithms, methods, functions, processes, flows, and procedures as described in the present disclosure.

The computer 802 also includes a database 806 that can hold data for the computer 802, another component communicatively linked to the network 803 (whether illustrated or not), or a combination of the computer 802 and another component. For example, database 806 can be an in-memory, conventional, or another type of database storing data consistent with the present disclosure. In some implementations, database 806 can be a combination of two or more different database types (for example, a hybrid in-memory and conventional database) according to particular needs, desires, or particular implementations of the computer 802 and the described functionality. Although illustrated as a single database 806 in FIG. 8, two or more databases of similar or differing types can be used according to particular needs, desires, or particular implementations of the computer 802 and the described functionality. While database 806 is illustrated as an integral component of the computer 802, in alternative implementations, database 806 can be external to the computer 802. As illustrated, the database 806 holds the previously described data 816 including, for example, multiple streams of data from various sources, such as measurement data in the form measurement logs, as shown in FIG. 1.

The computer 802 also includes a memory 807 that can hold data for the computer 802, another component or components communicatively linked to the network 803 (whether illustrated or not), or a combination of the computer 802 and another component. Memory 807 can store any data consistent with the present disclosure. In some implementations, memory 807 can be a combination of two or more different types of memory (for example, a combination of semiconductor and magnetic storage) according to particular needs, desires, or particular implementations of the computer 802 and the described functionality. Although illustrated as a single memory 807 in FIG. 8, two or more memories 807 or similar or differing types can be used according to particular needs, desires, or particular implementations of the computer 802 and the described functionality. While memory 807 is illustrated as an integral component of the computer 802, in alternative implementations, memory 807 can be external to the computer 802.

The application 808 is an algorithmic software engine providing functionality according to particular needs, desires, or particular implementations of the computer 802, particularly with respect to functionality described in the present disclosure. For example, application 808 can serve as one or more components, modules, or applications. Further, although illustrated as a single application 808, the application 808 can be implemented as multiple applications 808 on the computer 802. In addition, although illustrated as integral to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion or management circuits (including recharging, standby, or another power management functionality). In some implementations, the power-supply 814 can include a power plug to allow the computer 802 to be plugged into a wall socket or another power source to, for example, power the computer 802 or recharge a rechargeable battery.

There can be any number of computers 802 associated with, or external to, a computer system containing computer 802, each computer 802 communicating over network 803. Further, the term "client," "user," or other appropriate terminology can be used interchangeably, as appropriate, without departing from the scope of the present disclosure. Moreover, the present disclosure contemplates that many users can use one computer 802, or that one user can use multiple computers 802.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware-and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/−R, DVD-RAM, DVD-ROM, HD-DVD, and BLURRY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used b the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802,20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any subcombination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method to improve a computational accuracy and a computation time for predicting a fluid type within an unconventional tight reservoir, the computer-implemented method comprising:
accessing a plurality of measurement logs encoding measurements taken from more than one well location of the unconventional tight reservoir, wherein the plurality of measurement logs comprise a neutron log, a gamma ray (GR) log, a log of bulk density, a log of sonic slowness, a log of resistivity, and a log of photoelectric measurements;
in response to determining that a measured resistivity from the log of resistivity exceeds 31.62MΩ, determining, based on the plurality of measurement logs, a plurality of parameters that characterize a corresponding set of reservoir properties without determining an elastic rock property or a seismic velocity at the more than one well location of the unconventional tight reservoir;
based on a portion of the plurality of parameters, calculating a compressional formation slowness and a shear formation slowness at the more than one well location of the unconventional tight reservoir; and
predicting the fluid type at the more than one well location of the unconventional tight reservoir based on combining a ratio of the compressional formation slowness and the shear formation slowness with at least one of the plurality of parameters such that the fluid type is classified into one of two or more distinct categories and a production of hydrocarbon at unconventional tight reservoir is adjusted according to the classified fluid type, wherein the unconventional tight reservoir is characterized by the measured resistivity exceeding 31.62MΩ.

2. The computer-implemented method of claim 1, wherein the plurality of parameters comprise: a bulk density, and a resistivity.

3. The computer-implemented method of claim 1, wherein the plurality of measurement logs are based on gamma ray measurements performed at the more than one well location of the unconventional tight reservoir.

4. The computer-implemented method of claim 1, wherein combining the compressional formation slowness and the shear formation slowness with at least one of the plurality of parameters comprises:
cross plotting a parameter from the plurality of parameters with a metric that is based on the compressional formation slowness and the shear formation slowness.

5. The computer-implemented method of claim 4, wherein the metric comprises the ratio of the compressional formation slowness and the shear formation slowness.

6. The computer-implemented method of claim 4, wherein predicting a fluid type at the more than one well location of the unconventional tight reservoir comprises:
performing a classification of the fluid type by generating lines of regression based on the cross plotting in which data corresponding to the two or more distinct categories are clustered around separate lines of regression.

7. The computer-implemented method of claim 1, further comprising:
calibrating at least one the plurality of parameters to core sample measurements, wherein the core sample measurements comprise: a porosity measurement, and a saturation measurement, and
wherein the core sample measurements are based on nuclear magnetic resonance (NMR) of core samples taken at the more than one well location of the reservoir.

8. The computer-implemented method of claim 1, further comprising:
applying one or more environmental corrections to the plurality of measurement logs before determining the plurality of parameters.

9. A computer system comprising one or more processors configured to perform operations of:
accessing a plurality of measurement logs encoding measurements taken from more than one well location of an unconventional tight reservoir, wherein the plurality of measurement logs comprise a neutron log, a gamma ray (GR) log, a log of bulk density, a log of sonic slowness, a log of resistivity, and a log of photoelectric measurements;
in response to determining that a measured resistivity from the log of resistivity exceeds 31.62MΩ, determining, based on the plurality of measurement logs, a plurality of parameters that characterize a corresponding set of reservoir properties without determining an elastic rock property or a seismic velocity at the more than one well location of the unconventional tight reservoir;
based on at least a portion of the plurality of parameters, calculating a compressional formation slowness and a shear formation slowness at the more than one well location of the unconventional tight reservoir; and
predicting a fluid type at the more than one well location of the reservoir based on combining a ratio of the compressional formation slowness and the shear formation slowness with at least one of the plurality of parameters such that the fluid type is classified into one of two or more distinct categories and a production of hydrocarbon at unconventional tight reservoir is adjusted according to the classified fluid type, wherein the unconventional tight reservoir is characterized by the measured resistivity exceeding 31.62MΩ.

10. The computer system of claim 9, wherein the plurality of parameters comprise: a bulk density, and a resistivity.

11. The computer system of claim 9, wherein the plurality of measurement logs are based on gamma ray measurements performed at the more than one well location of the reservoir.

12. The computer system of claim 9, wherein combining the compressional formation slowness and the shear formation slowness with at least one of the plurality of parameters comprises:
cross plotting a parameter from the plurality of parameters with a metric that is based on the compressional formation slowness and the shear formation slowness.

13. The computer system of claim 12, wherein the metric comprises the ratio of the compressional formation slowness and the shear formation slowness.

14. The computer system of claim 12, wherein predicting a fluid type at the more than one well location of the reservoir comprises:
performing a classification of the fluid type by generating lines of regression based on said cross plotting in which data corresponding to the two or more distinct categories are clustered around separate lines of regression.

15. The computer system of claim 9, wherein the operations further comprise:

calibrating at least one the plurality of parameters to core sample measurements, wherein the core sample measurements comprise: a porosity measurement, and a saturation measurement, and wherein the core sample measurements are based on nuclear magnetic resonance (NMR) of core samples taken at the more than one well location of the reservoir.

16. The computer system of claim 9, wherein the operations further comprise:

applying one or more environmental corrections to the plurality of measurement logs before determining the plurality of parameters.

17. A non-transitory computer-readable medium comprising software instructions that, when executed by a computer processor, cause the computer processor to perform operations of:

accessing a plurality of measurement logs encoding measurements taken from more than one well location of an unconventional tight reservoir, wherein the plurality of measurement logs comprise a neutron log, a gamma ray (GR) log, a log of bulk density, a log of sonic slowness, a log of resistivity, and a log of photoelectric measurements;

in response to determining that a measured resistivity from the log of resistivity exceeds 31.62MΩ, determining, based on the plurality of measurement logs, a plurality of parameters that characterize a corresponding set of reservoir properties without determining an elastic rock property or a seismic velocity;

based on at least a portion of the plurality of parameters, calculating a compressional formation slowness and a shear formation slowness at the more than one well location of the unconventional tight reservoir; and predicting a fluid type at the more than one well location of the reservoir based on combining a ratio of the compressional formation slowness and the shear formation slowness with at least one of the plurality of parameters such that the fluid type is classified into one of three or more distinct categories and a production of hydrocarbon at unconventional tight reservoir is adjusted according to the classified fluid type, wherein the unconventional tight reservoir is characterized by the measured resistivity exceeding 31.62MΩ.

18. The non-transitory computer-readable medium of claim 17, wherein the operations further comprise:

calibrating at least one the plurality of parameters to core sample measurements, wherein the core sample measurements comprise: a porosity measurement, and a saturation measurement, and wherein the core sample measurements are based on nuclear magnetic resonance (NMR) of core samples taken at the more than one well location of the reservoir.

* * * * *

UNITED STATES PATENT AND TRADEMARK OFFICE
CERTIFICATE OF CORRECTION

PATENT NO. : 11,892,590 B2
APPLICATION NO. : 17/173360
DATED : February 6, 2024
INVENTOR(S) : Mohamed Amine Haceb It is certified that error appears in the above-identified patent and that said Letters Patent is hereby corrected as shown below:

On the Title Page

Column 2, item (56) Other Publications of Line 2, please replace "Dashti; Josimar" with
-- Dashti; --.

In the Claims

In Column 17, Line 66, Claim 7, please replace "one" with -- one of --.

In Column 19, Line 1, Claim 15, please replace "one" with -- one of --.

In Column 20, Line 20, Claim 18, please replace "one" with -- one of --.

Signed and Sealed this
Twelfth Day of November, 2024

*Katherine Kelly Vidal*

Katherine Kelly Vidal
*Director of the United States Patent and Trademark Office*